United States Patent [19]

Matsushita et al.

[11] Patent Number: 4,880,937

[45] Date of Patent: Nov. 14, 1989

[54] METHOD OF PRODUCING ALCOHOL COMPOUNDS

[75] Inventors: Hajime Matsushita, Yokohama; Makoto Shibagaki, Kawasaki; Kyoko Takahashi, Tokyo, all of Japan

[73] Assignee: Japan Tobacco, Inc., Tokyo, Japan

[21] Appl. No.: 157,246

[22] Filed: Feb. 18, 1988

[30] Foreign Application Priority Data

Mar. 3, 1987 [JP] Japan ................................ 62-46706

[51] Int. Cl.[4] ................. C07D 213/30; C07C 31/135; C07C 33/00; C07C 29/136
[52] U.S. Cl. .................................. 546/344; 568/814; 568/831; 568/877
[58] Field of Search ............... 546/344; 568/814, 877, 568/881, 831

[56] References Cited

FOREIGN PATENT DOCUMENTS 57-40444  3/1982  Japan ...................................... 560/72
57-130954 8/1982  Japan ..................................... 560/237

OTHER PUBLICATIONS

"Reactions of Titanium & Zirconium Alkoxides with Salicylaldehyde", Indian J. Chem., vol. 11, No. 8 (814–816).
J. Org. Chem., vol. 51, No. 2 (240–242).
Collection Czechoslov. Chem. Commun. vol. 45.
Nihon Kagakukai-shi (Japan Chemical Society Magazine, 1975, (12), pp. 2069–2073).

Primary Examiner—Alan L. Rotman
Attorney, Agent, or Firm—Nixon & Vanderhye

[57] ABSTRACT

An alcohol compound is produced by reducing a carboxylic acid or an ester thereof with an alcohol in the presence of a solid catalyst. The catalyst includes a hydrous metal oxide belonging to Group IV of the Periodic Table.

28 Claims, No Drawings

METHOD OF PRODUCING ALCOHOL COMPOUNDS

BACKGROUND OF THE INVENTION

1. Field of the Invention

The present invention relates to a method of producing alcohol compounds, and more particularly, to a method in which an alcohol is used as a reducing agent for reducing carboxylic acids or esters thereof so as to produce corresponding alcohol compounds.

2. Description of the related art including information disclosed under §§1.97-1.99

A reaction for converting a carboxylic acid or an ester thereof into its corresponding alcohol involves conversion of functional groups, which is important in the chemical industries. The known methods for the conversion include, for example, a method using a dissolved metal and a method of heterogeneous catalytic hydrogenation. A method using a hydride such as boron hydride or aluminum hydride or a derivative thereof as a reducing agent is also known to the art.

The method using a dissolved metal permits producing alcohol compounds at a relatively low cost and, thus, is widely employed. However, an active metal such as lithium or sodium is used in this method, making it necessary to handle the active metal very carefully. For example, these active metals vigorously react with water to generate hydrogen gas which is ignited easily. In addition, the method necessitates troublesome steps of treatment with water and extraction with an organic solvent for the recovery of the reaction products.

In the heterogeneous catalytic hydrogenation method, used is, for example, a ruthenium-based catalyst, a copper chromite-based catalyst or Raney nickel catalyst. However, a relatively high temperature/high pressure is required and the carboxylic acids/esters as the starting materials are restricted in this method, as described in, for example, "Reduction in Organic Chemistry" by Hadry.

The method using a hydride as a reducing agent can be widely used. However, the reducing agent used is costly and highly reactive with water, making it necessary to handle and preserve the reducing agent carefully. Also, the reaction in this method is generally so vigorous that the hydrogen gas produced in the reaction may possibly be ignited. Further, the method requires troublesome post-treatments to decompose the complex formed as an intermediate product and to extract the decomposed substances with an organic solvent.

SUMMARY OF THE INVENTION

An object of the present invention is to provide a safe method of producing alcohol compounds from carboxylic acids or esters thereof at a high yield without involving troublesome post-treatments.

According to the present invention, there is provided a method of producing alcohol compounds, comprising allowing a carboxylic acid or an ester thereof to contact with a reducing agent comprising an alcohol in the presence of a solid catalyst comprising a hydrous oxide of at least one element selected from the Group IV elements of the Periodic Table, thereby reducing the carboxylic acid or ester thereof inot its corresponding alcohol compound.

DESCRIPTION OF THE PREFERRED EMBODIMENTS

In the present invention, a carboxylic acid or an ester thereof is reduced to its corresponding alcohol compound by means of an alcohol acting as a reducing agent. A solid catalyst is used in the reducing reaction, including a hydrous oxide of at least one element (metal) selected from the Group IV elements of the Periodic Table. It is particularly desirable to use hydrous zirconium oxide, hydrous titanium oxide or hydrous tin oxide as the catalyst. These hydrous oxides may be used singularly or in combination. The "hydrous oxide" or "hydrous metal (e.g., zirconium) oxide" used herein is considered as having a metal-oxygen-metal bond, and, hydroxyl groups are also directly bonded to the metal atoms. Thus, it may be well said to be a partially dehydrated condensate of a metal hydroxide. The "hydrous oxide" is not intended to mean that the metal oxide contains water molecules such as the water of crystallization.

The hydrous metal oxide is a white, hard, non-crystalline or amorphous solid material and is insoluble in water, alcohol or other organic solvents so as to provide a stable heterogeneous catalytic system. The hydrous metal oxide can easily and cheaply be prepared by converting salts such as oxides and chlorides of group IV metal of the Periodic Table into hydroxides and subsequently heating these hydroxides under conditions which do not completely dehydrate the hydroxides. Although the hydroxides are completely dehydrated if heated at a temperature of 500° C. or more under the atmospheric pressure, they are partially dehydrated when heated at about 300° C. The weight of the metal hydroxide decreases by about 17% after an hour of heating, and thereafter substantial weight loss does not occur. The hydrous oxides of zirconium and tin can be obtained at a low cost whereas the earth is relatively abundant in zirconium and tin. The hydrous metal oxide may be pulverized or sieved after pulverization. It is also possible to have the pulverized hydrous metal oxide supported by, for example, alumina or activated carbon.

The inventors have found that hydrous metal oxide efficiently catalyzes the reduction of carboxylic acids or esters thereof with an alcohol into the corresponding alcohols to provide the corresponding alcohol compounds with a high yield, and that the hydrous metal oxide can be repeatedly used with satisfactory results.

The carboxylic acids or esters thereof which can be reduced into their corresponding alcohol compounds according to the present invention include chain carboxylic acids or esters thereof and cyclic (i.e., alicylic, aromatic and heterocyclic) carboxylic acids or esters thereof (formic acid being excluded). Examples of carboxylic acids or esters (carboxylic compound) are: acetic acid and its ester; propionic acid, caproic acid and their ethyl esters; capric acid and its ethyl ester; benzoic acid and its ethyl ester; cyclohexyl carboxylic acid and its ethyl ester; 2-methyl valeric acid and its ethyl ester; nicotinic acid, isonicotinic acid and their methyl esters; lauric acid, myristic acid, palmitic acid, stearic acid and their ethyl esters; and unsaturated aliphatic acids such as acrylic acid and oleic acid as well as their respective ethyl esters.

Any of aliphatic, aromatic and alicyclic alcohols can be used as the reducing agent (hydrogen source) in the present invention. In view of cost and reducing efficiency, it is desirable to use alkanols having 2 to 6 carbon atoms such as ethanol, propanol and butanol, particularly branched alkanols, or benzyl alcohol. It is most desirable to use isopropanol.

In the present invention, the reduction can be carried out either in a gaseous phase or a liquid phase. In the case of the gaseous phase reduction, a reaction tube loaded with the solid catalyst is heated to a reducing temperature, and a mixture of a carboxylic acid or ester thereof and an alcohol acting as a reducing agent is introduced into the catalyst layer or bed in the reaction tube. The reaction mixture may be carried with an inert carrier gas such as nitrogen gas or helium gas may also be introduced, as desired. The reaction temperature generally ranges between 250° C. and 450° C., desirably, between 280° C. and 350° C. If the reaction temperature is lower than 250° C., the product of the reaction consists mainly of an ester between the carboxylic acid and the alcohol used as the reducing agent. On the other hand, if the temperature is higher than 450° C., decomposing occurs as the main reaction. The outlet port of the reaction tube is cooled by cooling means such as water or ice so as to condense the effluents containing the reaction products, unreacted reactants, etc. The desired reaction product, i.e., alcohol compound, can be isolated by distilling the condensed effluents.

The molar ratio of the carboxylic acid or its ester to the reducing agent alcohol is usually 1:5 to 200, desirably, 1:10 to 100.

Where the reduction is carried out in liquid phase, the carboxylic acid or ester thereof is mixed with the reducing agent in a molar ratio as in the gaseous phase reaction described above. The hydrous metal oxide catalyst is added in an amount of 1 to 3 g/10 ml of the liquid phase mixture, and the reducing reaction is carried out for at least two hours, desirably, for 5 hours or more at a temperature of the gaseous phase reaction. A solvent inert to the reaction, e.g., tetrahydrofuran, may be added, as desired, to the reaction system for the purpose of, for example, dilution. It is desirable to carry out the liquid phase reaction within an autoclave. After the reaction, the catalyst is removed by means of, for example, filtration. Then, the alcohol compounds formed by the reducing reaction are isolated by distilling the reaction mixture.

In the gaseous phase or liquid phase reducing reaction described above, an ester may be formed as a by-product between the carboxylic acid and the alcohol used as the reducing agent. However, the by-product ester may also be reduced in the reaction to provide the corresponding alcohol compound.

CATALYST MANUFACTURING EXAMPLE A 200 g of zirconium oxychloride octahydrate was dissolved in 10 liters of deionized water. Then, a 1 N aqueous solution of sodium hydroxide was slowly added to the resultant solution while stirring the solution to adjust the pH value of the solution to 6.8. The resultant hydrated gel was filtered to remove the excess aqueous solution of salts, followed by a repeated washing of the gel with deionized water until chlorine ions were no longer detected in the wash liquid.

The gel thus obtained was cut into small pieces with a knife and left in a room for air drying. The dried gel was put in deionized water, with the result of the gel being vigorously pulverized to provide a granular material consisting of various size grains. After the grains were separated from the water by filtration, they were dried again at room temperature to obtain 90 g of a granular material. The granular material was classified, and grains of 24 to 60 meshes were collected and heated for 3 hours at 300° C. within a dryer. During the heating, a weight loss of about 17% was observed. Thus, a desired hydrous zirconium oxide catalyst was obtained.

CATALYST MANUFACTURING EXAMPLE B 190 g of titanium tetrachloride was added to 10 liters of deionized water while stirring the water. Then, a 28% aqueous ammonia was slowly added to the solution to adjust the pH value of the solution to 7. The resultant gel was filtered with a Buchner funnel, followed by repeatedly washing the gel with deionized water until chlorine ions were no longer detected in the was liquid.

The gel thus obtained was cut into small pieces with a knife and left in a room for air drying. The dried gel was put in deionized water, with the resulting gel being vigouously pulverized to provide a granular material consisting of various size grains. After the grains were separated from the water by filtration, they were dried again at room temperature in an enameled vat to obtain 30 g of a granular material. The granular material was classified, and grains of 24 to 60 meshes were collected and heated for 3 hours at 300° C. within a dryer. During the heating, a weight loss of about 17% was observed. Thus, a desired hydrous titanium oxide catalyst was obtained.

CATALYST MANUFACTURING EXAMPLE C 261 g of tin tetrachloride was added to 4 liters of deionized water while stirring the water. Then, a 28% aqueous ammonia was slowly added to the solution to adjust the pH value of the solution to 7. The resultant gel was filtered with a Buchner funnel, followed by repeatedly washing the gel with deionized water until chlorine ions were no longer detected in the washing liquid.

The gel thus obtained was cut into small pieces with a knife and left in a room for air drying. The dried gel ws put in deionized water, with the resulting gel being vigorously pulverized to provide a granular material consisting of various size grains. After the grains were separated from the water by filtration, they were dried again at room temperature in an enameled vat to obtain 141 g of a granular material. The granular material was classified, and grains of 24 to 60 meshes were collected and heated for 3 hours at 300° C. in a dryer. During the heating, a weight loss of about 17% was observed. Thus, a desired hydrous tin oxide catalyst was obtained.

EXAMPLES 1 TO 5

A heat-resistant glass tube with a 4 mm inner diameter, 6 mm outer diameter and 50 cm length was charged with 2 g of the hydrous zirconium oxide catalyst prepared in Example A such that the catalyst was fixed within the glass tube to form a 15 mm thick layer. The glass tube charged with the catalyst was heated within an electric furnace to 300° C.

On the other hand, a reactant mixture was prepared by dissolving 10 millimols of cyclohexane carboxylic acid in 50 ml (650 millimols) of isopropanol. The resultant solution was introduced into the glass tube by injecting the solution at room temperature with a micro feeder at the rate of 5 ml/hour into a nitrogen gas stream (carrier gas) flowing at the rate of 1 ml/sec. The gaseous stream passing through the catalyst layer within the glass tube was condensed by water-cooling and collected at the outlet port of the glass tube. The collected reaction product was analyzed by gas chromatography to determine the conversion rate, i.e., percentage of conversion from the raw material carboxylic acid into reaction products, and the selectivity, i.e., percentage of the formed alcohol in the reaction products (Example 1). Table 1 shows the results.

Additional examples were conducted as in Example 1, except that n-butyric acid, pivaric acid, 2-methyl pentanoic acid and benzoic acid were used as the raw material carboxylic acids (Examples 2 to 5) in place of the cyclohexane carboxylic acid used in Example 1. Table 1 also shows the results of these examples.

was analyzed by gas chromatography, with the results shown in Table 3.

TABLE 3

| Reaction Temp. | ⬡-CH₂OH | ⬡-COOCH(CH₃)₂ | Unreacted ⬡-COOH |
|---|---|---|---|
| 200° C. | 0 | 81 | 19 |
| 250° C. | 7 | 93 | 0 |
| 280° C. | 42 | 58 | 0 |
| 300° C. | 94 | 6 | 0 |
| 330° C. | 85 | 0 | 0 |
| 380° C. | 49 | 0 | 0 |
| 450° C. | 20 | 0 | 0 |

TABLE 1

| Example No. | Carboxylic acid | Formed Alcohol | Conversion rate (%) | Selectivity (%) |
|---|---|---|---|---|
| 1 | cyclohexyl-COOH | cyclohexyl-CH₂OH | 100 | 94 |
| 2 | propyl-COOH | butyl-OH | 100 | 78 |
| 3 | (CH₃)₃C-COOH | (CH₃)₃C-CH₂OH | 100 | 98 |
| 4 | 2-methylpentyl-COOH | 2-methylpentyl-CH₂OH | 100 | 84 |
| 5 | phenyl-COOH | phenyl-CH₂OH | 93 | 63 |

EXAMPLES 6 TO 8

The same procedures were followed as in Example 1, except that ethyl n-caprate, ethyl benzoate and ethyl n-hexanoate were used in place of the cyclohexane carboxylic acid used in Example 1. Table 2 shows the results of these experiments.

EXAMPLE 10

The reaction between cyclohexane carboxylic acid and isopropanol was conducted under the same conditions as in Example 1, except that hydrous titanium oxide catalyst prepared in Example B was used in place of the hydrous zirconium oxide catalyst used in Exam-

TABLE 2

| Example No. | Carboxylic acid | Formed Alcohol | Conv. rate | Selectivity |
|---|---|---|---|---|
| 6 | CH₃(CH₂)₈COOC₂H₅ | CH₃(CH₂)₉OH | 92% | 95% |
| 7 | phenyl-COOC₂H₅ | phenyl-CH₂OH | 100% | 51% |
| 8 | hexyl-COOC₂H₅ | hexyl-CH₂OH | 97% | 89% |

EXAMPLE 9

The reaction between cyclohexane carboxylic acid and isopropanol was conducted under the same conditions as in Example 1, except that the temperature in the electric furnace was altered a shown in Table 3. The rate of reaction products at each reaction temperature ple 1. It was discovered by gas chromatography that cyclohexyl methanol was formed at a conversion rate of 18% and selectivity of 71%. The isopropanol dehydration is considered to have preceded the reduction, leading to the low conversion rate.

Similarly, an additional experiment was conducted, except the reaction temperature was set at 200° C. In this case, the product isopropyl cyclohexane carboxylate was obtained at a conversion rate of 56% and a selectivity of 99%.

EXAMPLE 11

The reaction between cyclohexane carboxylic acid and isopropanol was conducted under the same conditions as in Example 1, except that 1 g of hydrous tin oxide catalyst prepared in Example C was used in place of 2 g of the hydrous zirconium oxide catalyst used in Example 1. It was discovered by gas chromatography that cyclohexyl methanol was formed at a conversion rate of 95% and selectivity of 39%. Isopropyl cyclohexane carboxylic acid was also obtained as a by-product in an amount of 41%.

EXAMPLE 12

The reaction was conducted under the same conditions as in Example 1, except that the hydrous titanium oxide obtained in Example B was used in place of the hydrous zirconium oxide used in Example 1 and tht ethyl n-caproate was used in place of cyclohexane carboxylic acid used in Example 1. The reaction product was analyzed by gas chromatography. It was discovered that decyl alcohol was formed at a conversion rate of 100% and a selectivity of 22%, the remaining reaction product being isopropyl n-caproate.

EXAMPLE 13

The reaction was conducted under the same conditions as in Example 1, except that the hydrous tin oxide obtained in Example C was used in place of the hydrous zirconium oxide used in Example 1 and that ethyl n-caproate was used in place of cyclohexane carboxylic acid used in Example 1. The reaction product was analyzed by gas chromatography. The conversion rate was found to be 88%. Also, the reaction product was found to contain 56% of n-hexanol and 44% of isopropyl n-caproate.

EXAMPLES 14-18

The reaction was conducted under the same conditions as in Example 1, except that benzyl alcohol was used in place of isopropanol of Example 1. In short, the reaction occured between benzyl alcohol and cyclohexane carboxylic acid in Example 14. Table 4 shows the results with respect to the conversion rate and selectivity.

Additional experiments were similarly conducted, except that 2-methyl pentanoic acid, pivaric acid, ethyl caprate, and ethyl benzoate were respectively used (Examples 15-18) in place of cyclohexane carboxylic acid of Example 14. Table 4 also shows the results of Examples 15-18.

TABLE 4

| Example No. | Starting material | Reaction product | Conv. rate | Selectivity |
| --- | --- | --- | --- | --- |
| 14 | ⬡—COOH | ⬡—CH₂OH | 100% | 89.2% |
| 15 | ⌒⌒⋎COOH | ⌒⌒⋎CH₂OH | 100% | 96% |
| 16 | +COOH | +CH₂OH | 98% | 92% |
| 17 | ⌒⌒⌒⌒⌒COOC₂H₅ | ⌒⌒⌒⌒⌒OH | 83% | 95% |
| 18 | ⬡—COOC₂H₅ | ⬡—CH₂OH | 100% | 62% |

EXAMPLES 19-21

A stainless steel autoclave having an inner volume of 100 ml was charged with 5 g of the hydrous zirconium oxide obtained in Example A, 5 millimols of cyclohexane carboxylic acid and 30 millimols of isopropanol, and the reaction occured at 280° C. over a 5 hour period. Following the reaction, the hydrous zirconium oxide was removed from the reaction mixture by filtration and the residual mixture was subjected to gas chromatography to determine the conversion rate and composition of the mixture (Example 19).

Additional experiments were similarly conducted, except that n-hexanoic acid and ethyl n-hexanoate were used respectively (Examples 20 and 21) in place of cyclohexane carboxylic acid of Example 19. Table 5 shows the results.

TABLE 5

| Example No. | Carboxylic acid/ester | Conv. rate | Formed products | | |
|---|---|---|---|---|---|
| 19 | C6H11-COOH (cyclohexane-COOH) | 100% | C6H11-CH2OH 66% | | C6H11-COOCH(CH3)2 28% |
| 20 | ~~~COOH | 100% | ~~~OH 71% | | ~~~COOCH(CH3)2 11% |
| 21 | ~~~COOC2H5 | 100% | ~~~OH 75% | | ~~~COOCH(CH3)2 13% |

As described above in detail, a reducing reaction of a carboxylic acid or ester thereof with an alcohol is effectively promoted in the present invention by the solid catalyst, making it possible to obtain an alcohol compound at a relatively high yield. It is important to note that the hydrous metal oxide used in the present invention provides a heterogeneous catalytic sytem. Thus, the catalyst and the formed alcohol can be easily recovered after the reaction. Further, the catalyst used in the present invention is free from swelling and eluation and exhibits a high resistance to heat and solvents. It follows that the catalyst can be used repeatedly in either the gaseous phase or liquid phase reducing reactions.

What is claimed is:

1. A method of producing an alcohol compound, comprising, allowing a carboxylic acid compound selected from the group consisting of $C_2-C_{18}$ unsubstituted chain carboxylic acid, 2-methyl-pentanoic, pivaric, acrylic, oleic, cyclohexane carboxylic acid benzoic acid or their ethyl ester, nicotinic acid, isonicotinic acid or their methyl ester thereof to come into contact with a reducing agent consisting of an alcohol selected from the group consisting of alkanols having 2 to 6 carbon atoms and benzyl alcohol, in the presence of a solid catalyst consisting of a hydrous oxide selected from the group consisting of hydrous zirconium oxide, hydrous titanium oxide and hydrous tin oxide, thereby reducing said carboxylic compound to its corresponding alcohol compound.

2. A method according to claim 1, wherein said carboxylic compound is selected from the group consisting of acetic acid; propionic butyric acid, caproic acid or their ethyl esters; capric acid or its ethyl ester; benzoic acid or its ethyl ester; cyclohexyl carboxylic acid or its ethyl ester; 2-methyl valeric acid or its ethyl ester; nicotinic acid, isonicotinic acid or their methyl esters; lauric acid, myristic acid, palmitic acid, stearic acid or their ethyl esters; and acrylic acid and oleic acid and their ethyl esters.

3. A method according to claim 1, wherein said alkanol is a branched alkanol.

4. A method according to claim 1, wherein said alcohol reducing agent is isopropaol.

5. A method according to claim 1, wherein said carboxylic compound is contacted with said alcohol reducing agent in a molar ratio of 1 : 5 to 1: 200.

6. A method according to claim 1, wherein the reducing reaction is carried out at 250 to 450° C.

7. A method according to claim 1, wherein the reducing reaction is carried out in a gaseous phase.

8. A method according to claim 1, wherein the reducing reaction is carried out in a liquid phase.

9. A method according to claim 1, wherein the carboxylic acid has 2 to 18 carbon atoms.

10. A method according to claim 1, wherein the carboxylic acid has 40 to 10 carbon atoms.

11. A method of producing an alcohol compound, comprising the steps of:
preparing a mixture consisting of a carboxylic acid compound selected from the group consisting of $C_2-C_{18}$ unsubstituted chain acid, 2-methylpentanoic, pivaric, acrylic, oleic, cyclohexanecarboxylic acid, benzoic acid or their ethylester, nicotinic acid, isonicotinic acid or their methylester thereof, (ii) a reducing agent comprising an alcohol selected from the group consisting of alkanols having 2 to 6 carbon atoms and benzyl alcohol, and (iii) a solid catalyst consisting of a hydrous oxide selected from the group consisting of hydrous zirconium oxide, hydrous titanium oxide and hydrous tin oxide;
placing said mixture under reducing conditions so as to reduce said carboxylic compound to an alcohol compound which corresponds to said carboxylic compound, by means of said reducing agent;
removing said solid catalyst from the reaction mixture; and
recovering the formed alcohol compound from the mixture after removal of the solid catalyst.

12. A method according to claim 11, wherein said reducing conditions include heating said mixture to 250° to 450° C.

13. A method according to claim 11, wherein said alkanol is a branched alkanol.

14. A method according to claim 13, wherein said alcohol reducing agent is isopropanol.

15. A method according to claim 11, wherein said carboxylic compound and said alcohol reducing agent are used in a molar ratio of 1:5 to 1:200.

16. A method according to claim 15, wherein said caatalyst is used in an amount of 1 to 3 g/10 ml of the sum of said carboxylic compound and said reducing agent alcohol.

17. A method according to claim 11, wherein the reducing reaction is carried out within an autoclave.

18. A method according to claim 11, wherein the carboxylic acid has 2 to 18 carbon atoms.

19. A method according to claim 11, wherein the carboxylic acid has 4 to 10 carbon atoms.

20. A method according to claim 11, wherein said carboxylic compound is selected from the group consisting of acetic acid, propionic acid or its ethyl ester; butyric acid, or its ethyl ester; caproic acid or its ethyl ester; capric acid its ethyl ester; benzoic acid or its ethyl ester; cyclohexyl carboxylic acid or its ethyl ester; 2-methyl valeric acid and its ethyl ester; nicotinic acid or its methyl ester; isonicotinic acid and its methyl ester; lauric acid or its ethyl ester; myristic acid or its ethyl ester; palmitic acid and its ethyl ester; stearic acid or its ethyl ester. acrylic acid or its ethyl ester; or oleic acid or its ethyl ester.

21. A method of producing an alcohol compound, comprising the steps of:
placing a mixture consisting of a (i) a carboxylic acid compound selected from the group consisting of $C_2$-$C_{18}$ unsubstituted chain acid, 2-methylpentanoic, pivaric, acrylic, oleic, cyclohexanecarboxylic acid, benzoic acid or their methyl ester thereof and (ii) a reducing agent consisting of an alcohol selected from the group consisting of alkanols having 2 to 6 carbon atoms and benzyl alcohol, under evaporation conditions;
bringing the evaporated mixture into contact with a solid catalyst consisting of hydrous oxide selected from the group consisting of hydrous zirconium oxide, hydrous titanium oxide and hydrous tin oxide so as to reduce said carboxylic compound to its corresponding alcohol compound by means of said reducing agent;
cooling the gaseous phase reaction mixture containing the formed alcohol compound in order to condense the reaction mixture; and
recovering the formed alcohol compound from the condensate.

22. A method according to claim 21, wherein said alkanol is a branched alkanol.

23. A method according to claim 21, wherein isopropanol is used as said alcohol reducing agent.

24. A method according to claim 21, wherein said carboxylic compound and said alcohol reducing agent are used in a molar ratio of 1:5 to 1:200.

25. A method according to claim 21, wherein the carboxylic acid has 2 to 18 carbon atoms.

26. A method according to claim 21, wherein the carboxylic acid has 4 to 10 carbon atoms.

27. A method according to claim 21, wherein said carboxylic compound is selected from the group consisting of acetic acid and its ester; propionic acid and its ester; butyric acid and its ester; caproic acid and its ester; capric acid and its ethyl ester; benzoic acid and its ethyl ester; cyclohexyl carboxylic acid and its ethyl ester; 2-methyl valeric acid and its ethyl ester; nicotinic acid and its methyl ester; isonicotinic acid and its methyl ester; lauric acid and its ethyl ester; myristic acid and its ethyl ester; palmitic acid and its ethyl ester; stearic acid and its ethyl ester; acrylic acid and its ethyl ester; and oleic acid and its ethyl ester.

28. A method according to claim 21, wherein said mixture is contacted with said solid catalyst at 250° to 450° C.

* * * * *